United States Patent
Vincent et al.

(10) Patent No.: US 8,694,098 B2
(45) Date of Patent: Apr. 8, 2014

(54) IMPLANTABLE DEFIBRILLATOR/CARDIOVERTER MEDICAL DEVICE WITH A DYNAMICALLY ADJUSTABLE THRESHOLD FOR VENTRICULAR DETECTION

(71) Applicant: Sorin CRM SAS, Clamart Cedex (FR)

(72) Inventors: Elodie Vincent, Antony (FR);
Marie-Anne Euzen, Bièvres (FR);
Marcel Limousin, Paris (FR)

(73) Assignee: Sorin CRM SAS, Clamart Cedex (FR)

( * ) Notice: Subject to any disclaimer, the term of this patent is extended or adjusted under 35 U.S.C. 154(b) by 0 days.

(21) Appl. No.: 13/683,839

(22) Filed: Nov. 21, 2012

(65) Prior Publication Data
US 2013/0131747 A1    May 23, 2013

(30) Foreign Application Priority Data
Nov. 22, 2011    (FR) ...................................... 11 60668

(51) Int. Cl.
*A61N 1/00*    (2006.01)
(52) U.S. Cl.
USPC ............................................................ 607/18
(58) Field of Classification Search
USPC ............................................................ 607/14
See application file for complete search history.

(56) References Cited

U.S. PATENT DOCUMENTS

| | | | |
|---|---|---|---|
| 5,411,533 A | 5/1995 | Dubreuil et al. | |
| 5,868,793 A | 2/1999 | Nitzsche et al. | |
| 6,714,820 B2 | 3/2004 | Casset et al. | |
| 7,756,570 B1 * | 7/2010 | Bornzin | 600/509 |
| 7,937,135 B2 | 5/2011 | Ghanem et al. | |
| 7,953,488 B2 | 5/2011 | Casavant et al. | |
| 7,968,068 B2 | 6/2011 | Bull et al. | |
| 2002/0165587 A1 | 11/2002 | Zhang et al. | |
| 2004/0015192 A1 | 1/2004 | Kim et al. | |
| 2004/0151192 A1 | 8/2004 | Trossen | |
| 2009/0326600 A1 | 12/2009 | Kracker | |
| 2011/0118804 A1 | 5/2011 | Henry et al. | |
| 2011/0172727 A1 | 7/2011 | Ousdigian | |
| 2011/0196247 A1 | 8/2011 | Cao et al. | |
| 2011/0230776 A1 | 9/2011 | Milpied et al. | |
| 2012/0022607 A1 | 1/2012 | Giorgis et al. | |

FOREIGN PATENT DOCUMENTS

| | | |
|---|---|---|
| EP | 0 838 235 A1 | 4/1998 |
| EP | 1 287 849 A1 | 3/2003 |
| EP | 1 857 142 A1 | 11/2007 |
| EP | 2 324 885 A1 | 5/2011 |
| EP | 2 412 401 A1 | 5/2011 |
| EP | 2 368 493 A1 | 9/2011 |
| WO | WO-93/02741 A1 | 2/1993 |

* cited by examiner

*Primary Examiner* — Robert N Wieland
(74) *Attorney, Agent, or Firm* — Foley & Lardner LLP

(57) ABSTRACT

Methods, devices, and processor-readable storage media are provided for detecting spontaneous ventricular events in a heart using implantable medical devices. A method in this context includes applying a sensitivity function to collected data to detect occurrence of ventricular events. The sensitivity function is based on an adjustable detection threshold. The method further includes determining whether noise is suspected to be present in the data and, if so, increasing the threshold. The method further includes providing a stimulation pulse to the heart when a ventricular event has not occurred after a predetermined escape interval and, following the stimulation pulse, applying a capture test to detect whether an induced depolarization has occurred. If induced polarization is not detected, the threshold is reduced, while the threshold is maintained if induced polarization is detected.

18 Claims, 3 Drawing Sheets

IMPLANTABLE DEFIBRILLATOR/CARDIOVERTER MEDICAL DEVICE WITH A DYNAMICALLY ADJUSTABLE THRESHOLD FOR VENTRICULAR DETECTION

CROSS-REFERENCE TO RELATED PATENT APPLICATIONS

This application claims benefit under 35 U.S.C. §119 to French application No. 1160668, filed Nov. 22, 2011, the entire contents of which are incorporated here by reference.

BACKGROUND OF THE INVENTION

The present invention relates to "active implantable medical devices," as defined by the 20 Jun. 1990 Directive 90/385/EEC of the Council of the European Communities. More particularly, the invention concerns implants that continuously monitor a patient's heart rhythm and deliver to the heart, if necessary, electrical pulses of stimulation, resynchronization, and/or defibrillation in the event of rhythm disorder detected by the device.

Illustrative of the devices in question is a device with an antitachycardia therapy mode, to terminate a tachyarrhythmia, which involves the controlled application of defibrillation shocks in the form of high-energy electrical pulses, and/or antitachycardia pacing (ATP) and the like. Such devices are called "implantable cardioverters/defibrillators" or "LCDs".

The decision to apply a therapy may be made by an algorithm configured to analyze the heart rhythm and detect a tachyarrhythmia episode. The various disorders may be detected and classified according to several discrimination criteria such as the ventricular frequency, the stability of ventricular intervals (RR intervals), the analysis of the atrio-ventricular association (revealed by the stability of the PR interval), the starting mode of the tachycardia (presence of a sudden acceleration and ventricular or atrial origin cavity) or the morphology of the intracardiac signal.

The rhythm analysis and, hence, the decision to deliver or not to deliver a therapy may be affected by artifacts collected by the lead, however. Indeed, these implants are sensitive to the detection of non-cardiac origin signals due to problems with the lead, to electromagnetic interference, or to the detection of myopotentials, etc. These phenomena are designated hereafter by the generic term of "noise."

Such phenomena are likely to generate artifacts, the detection of which by the implant may have very serious consequences. Thus, the detection of noise can result in the creation of a ventricular pause due to the inhibition of ventricular pacing, which may be symptomatic for dependent patients, or in the onset of delivering inappropriate defibrillation shocks.

Yet, the application of any defibrillation shock in a conscious patient is extremely painful and distressing, with the energy applied being far beyond the pain threshold. In addition, the application of a defibrillation shock is not without side effects on the heart rate (i.e., risk of development of secondary disorders), on the functional integrity of the myocardium, and in general on the physiological balance of the patient. It is important, therefore, to deliver such shocks appropriately.

Various techniques have been proposed to reduce the impact of noise, including the automatic adjustment of the sensitivity of the sensing amplifiers, or the automatic gain control of these amplifiers. Firstly, to detect ventricular fibrillation (VF), the signal level of which is low, it is necessary to have maximum sensitivity; otherwise there is the risk not to detect events that should have been ("sub-detections"). Secondly, however, the ventricular fibrillation signal amplitude (e.g., QRS complexes indicative of ventricular depolarization) may be at a variable level, intermediate between the noise and the sinus complex signals.

During detection of ventricular fibrillation, the detection of a possible noise thus is unavoidable. In other words, if the implant is programmed to a too high sensitivity value, that is to say, with a detection threshold too low, then ventricular arrhythmia episodes are properly detected but the increased sensitivity to noise greatly increases the risk of applying inappropriate and undesirable therapy (false positive situation, called oversensing).

Conversely, if the implant is programmed to a too low sensitivity value (i.e., with a detection threshold that is too high), then the actual episodes of ventricular arrhythmias may not be detected (i.e., a sub-detection, or false negative, situation), which for the patient can mean very serious consequences.

Because the detection of extrinsic noise usually is inevitable, the problem addressed by the present disclosure is to adjust the parameters of ventricular arrhythmia detection so as to discriminate noise from cardiac depolarizations, in order to avoid triggering inappropriate therapies or, conversely, inhibiting therapies that would have been justified.

Various proposals have been made in the prior art to try to find a solution to this problem:

(A) United States Published Application No. 2011/0172727 proposes, in cases of probable arrhythmias, to run an "inappropriate detection suspicion" algorithm, based on the number of short RR intervals detected, the coupling between the cavities (PR interval), the morphology of the ventricular depolarization signals, and the instability of the RR coupling. Upon actually suspect detection, the device increases the persistence, that is to say, the latency for the application of a therapy, or modifies the applied therapy (reduction in the number of shocks or changes in the sequence of ATP stimulation). The disadvantage of this technique is that, in case of noise detection, the consequences of inappropriate therapy are only reduced but this therapy is not prevented. In addition, the discrimination technique disclosed does not work in case of high amplitude sustained noise.

(B) U.S. Pat. No. 7,953,488 proposes, in case of detected noise or of ventricular undersensing, to perform a step of confirmation by operating a switch of the detection channel to verify that the noise is not present on the other channel. This technique obviously works in a situation in which noise is present on only one of two paths; otherwise, the risk of application of inappropriate therapy remains.

(C) U.S. Pat. No. 7,937,135 provides for adjusting the detection sensitivity according to the amplitude of the signal, on analyzed two ECG channels. In cases of suspected noise, a window is opened in which the morphology and the amplitude of the signal are analyzed. If noise is detected then the measured frequency is corrected (short couplings are disabled) to avoid inappropriate diagnosis. This technique is not suitable in cases of high amplitude noise. It also increases the risk of non-detection of ventricular fibrillation in case of an error on the discrimination between noise and VF.

(D) U.S. Pat. No. 7,756,570 relates to increasing of the detection sensitivity in the absence of noise and reducing the sensitivity when noise is detected. After a predetermined period (e.g., one or more stimulated cycles), the sensitivity returns to its minimum value, to check whether the noise still is present or whether an arrhythmia has not occurred in the meantime. The detection threshold is a function of the amplitude of the R wave. The amplitude threshold for the detection of noise is thus an adaptive, variable threshold, updated according to the level of the detected noise. The disadvantage of this technique is the delay that it introduces in the detection of an arrhythmia, due to the application of high sensitivity after a fixed period of time, with a risk of detecting noisy cycles when high sensitivity is restored (ventricular pause situation).

(E) United States Published Application No. 2002/0165587 operates in a manner comparable to (D), identifying at each cycle a noise level and a signal level and adjusting the detection threshold based on these respective levels. The same problems pertain, however. United States Published Application No. 2004/0015192 also describes the use of a variable dynamic threshold to improve the conditions for delivery of a defibrillation shock.

Other techniques have been proposed to reduce the impact of electromagnetic noise interferences. For instance, United States Published Application No. 2011/0196247 operates a counting of the signal fluctuations in a time window defined between two cardiac events and considers the presence of noise depending on the result of this counting. United States Published Application No. 2009/0326600 proposes, in case of suspected arrhythmias, an impedance measurement of the electrodes to discriminate between arrhythmia and noise.

SUMMARY OF THE INVENTION

One embodiment relates to a method for detecting spontaneous ventricular events in a heart by using an implantable device. The method includes: (A) using the implantable device to collect data relating to electrical activity of the heart; (B) applying a sensitivity function to the collected data to detect occurrence of ventricular events, wherein the sensitivity function is based on an adjustable detection threshold; (C) determining whether noise is suspected to be present in the collected data; (D) increasing the adjustable detection threshold upon determining that noise is suspected to be present in the collected data; (E) providing a stimulation pulse to the heart when a ventricular event has not occurred after a predetermined escape interval; and, following the stimulation pulse, (F) applying a capture test to detect whether an induced depolarization has occurred; (G) reducing the adjustable detection threshold when an induced depolarization is not detected based on the capture test; and (H) maintaining the adjustable detection threshold when an indicated depolarization is detected based on the capture test.

Another embodiment of the disclosure relates to an implantable device configured to detect spontaneous ventricular events in a heart. The implantable device includes a processor and a memory having instructions stored thereon that, when executed by the processor, cause the processor to: (A) collect data relating to electrical activity of the heart; (B) apply a sensitivity function to the collected data to detect occurrence of ventricular events wherein the sensitivity function is based on an adjustable detection threshold; (C) determine whether noise is suspected to be present in the collected data; (D) increase the adjustable detection threshold upon determining that noise is suspected to be present in the collected data; (E) provide a stimulation pulse to the heart when a ventricular event has not occurred after a predetermined escape interval; and, following the stimulation pulse, (F) apply a capture test to detect whether an induced depolarization has occurred; (G) reduce the adjustable detection threshold when an induced depolarization is not detected based on the capture test; and (H) maintain the adjustable detection threshold when an indicated depolarization is detected based on the capture test.

Yet another embodiment relates to a processor-readable storage medium having instructions stored thereon that, when executed by a processor of an implantable device, cause the implantable device to implement various operations. These operations include: (A) using the implantable device to collect data relating to electrical activity of the heart; (B) applying a sensitivity function to the collected data to detect occurrence of ventricular events, wherein the sensitivity function is based on an adjustable detection threshold; (C) determining whether noise is suspected to be present in the collected data; and (D) increasing the adjustable detection threshold upon determining that noise is suspected to be present in the collected data, (E) providing a stimulation pulse to the heart when a ventricular event has not occurred after a predetermined escape interval; and, following the stimulation pulse, (F) applying a capture test to detect whether an induced depolarization has occurred; (G) reducing the adjustable detection threshold when an induced depolarization is not detected based on the capture test; and (H) maintaining the adjustable detection threshold when an indicated depolarization is detected based on the capture test.

BRIEF DESCRIPTION OF THE DRAWINGS

Further features, characteristics, and advantages will become apparent from the following detailed description of preferred embodiments of the invention, made with reference to the annexed drawings, in which like reference characters refer to like elements and in which.

DETAILED DESCRIPTION OF THE PREFERRED EMBODIMENTS

Figure 1:
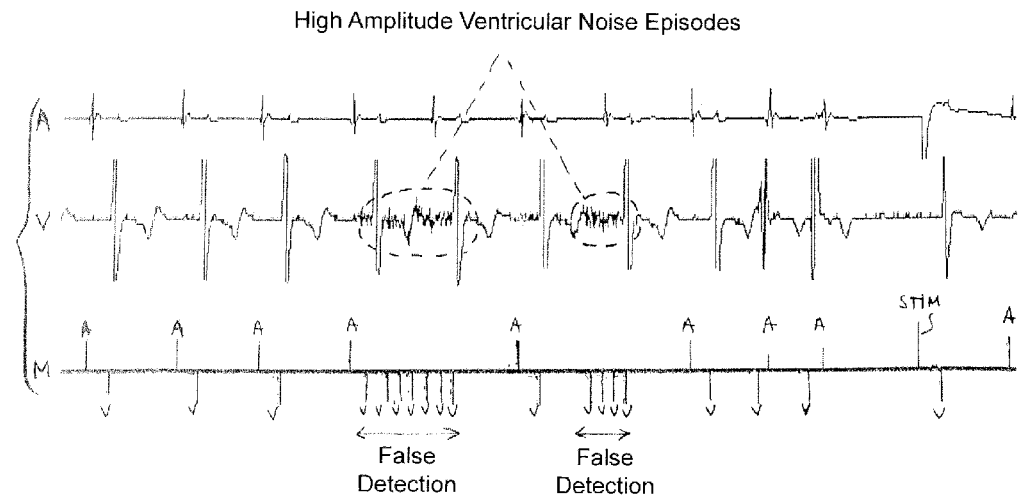
FIG. 1 is a set of timing diagrams illustrating the incidence of episodes of ventricular noise of high amplitude on the occurrence of false detections with implants according to an exemplary embodiment of the prior art.

With general reference to the drawings, devices and methods for detecting ventricular arrhythmias are provided that are illustrated by embodiments described below. In keeping with the invention, various embodiments can be configured to reduce the detection of ventricular noise while maintaining good detection of ventricular arrhythmias.

More specifically, the devices and methods of the invention detect occurrence of ventricular events based on data, relating to electrical activity of the heart, collected using an implantable device. The detection of the events can be performed using a sensitivity function that is based on an adjustable detection threshold. A low ventricular sensitivity (e.g., a relatively high detection threshold) may be initially utilized in an instance of suspected noise. A noise test may be used to determine whether noise is suspected to be present in the collected data. If noise is suspected to be present in the data, then the sensitivity can be reduced and the adjustable threshold can be increased to avoid oversensing. In various embodiments, the raising of the threshold level detection on noise detection may be gradual, may be stepwise over the duration of a retriggerable refractory period, or may go directly to a level that is based on the amplitude of the cycles for which the suspected noise has been detected.

A stimulation pulse may be triggered and provided by the implant in the case of under-detection due to lowered sensitivity. A capture test then may be used to determine whether an induced polarization has occurred following the stimulation pulse. If the stimulation occurs during an arrhythmia then it will not be effective. Depending on the result of the capture test, either (i) the sensitivity is kept low and the threshold is maintained relatively high (effective stimulation, indicating an absence of arrhythmia) or (ii) the sensitivity is increased and the threshold is lowered to avoid the risk of under-detection, because in that case the suspected noise actually is a ventricular arrhythmia episode (stimulation ineffective because of the arrhythmia). As noted, the lowering of the detection threshold in the absence of induced depolarization may be gradual, stepwise up to a preset limit value, or directly to a pre-programmed limit value.

With respect to its software aspects, the present disclosure puts forward exemplary embodiments that can be implemented by an appropriate programming of the controlling software of a known device, such as a cardiac pacemaker, a resynchronization device, or a defibrillator/cardioverter. Such devices may be configured, pursuant to the invention, to collect a signal provided by endocardial leads and/or one or more implanted sensors. In particular, embodiments of the present disclosure may be implemented using implantable devices such as those of the Paradym and Ovatio device families produced and marketed by Sorin CRM S.A.S. (Clamart, France), formerly known as ELA Medical (Montrouge, France).

Various operations of the exemplary methods described here may be implemented using software (e.g., using appropriate algorithms executed by a microcontroller or a digital signal processor). Exemplary devices of the present disclosure may include programmable microprocessor circuitry to receive, format, and process electrical signals collected (detected) by electrodes implanted and deliver stimulation pulses to these electrodes. By telemetry it is possible to transmit software that will be stored in a memory of an implantable device of the invention and then executed to implement the functions described here.

With reference to FIG. 1, the first two timing signals illustrate, respectively, atrial (A) and ventricular (V) electrograms (EGM) collected by an implant. The ventricular detection sensitivity (e.g., programmed by the physician, during implantation or later) is generally set at a level of about 0.4 mV. The timing diagram below illustrates the corresponding markers (M) delivered by the analysis algorithm of these EGM signals with atrial detection markers (A), ventricular detection markers (V) as well as markers of application of a stimulation triggered in the implant (STIM).

Note the presence on the ventricular signal of two episodes of ventricular noise of high amplitude. In some embodiments the noise may have a high amplitude, e.g., greater than 1 mV and up to 5 mV. Such noise may be incorrectly interpreted by the implant as ventricular fibrillation (e.g., a series of closely spaced V markers). Incorrectly interpreting the noise as ventricular fibrillation may inhibit stimulation, creating a ventricular pause for dependent patients, and may also trigger inappropriate therapy for the patient if it continues.

Figure 2:
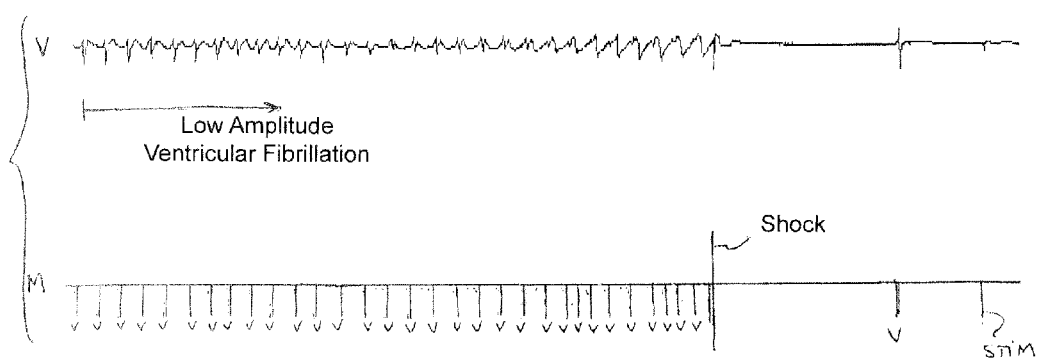
FIG. 2 is a set of timing diagrams illustrating a typical episode of ventricular fibrillation with low amplitude signals according to an exemplary embodiment.

FIG. 2 illustrates a typical situation of true ventricular fibrillation according to an exemplary embodiment. The illustrated V signal includes a succession of fast depolarizations. After analysis, the algorithm may decide to initiate therapy by application of a defibrillation shock, which may result in a return to normal sinus rhythm, if necessary with ventricular pacing.

A particular difficulty may arise when the ventricular fibrillation has low amplitude (e.g., a detected ventricular signal level on the order of 2 to 5 mV). To be sure to detect such arrhythmias, it is important to program the implant with a high sensitivity (low detection threshold). Yet, heightening the sensitivity of the implant also increases the risk of detection of ventricular noise, which could cause the implant to trigger inappropriate therapies deleterious to the patient.

Figure 3:
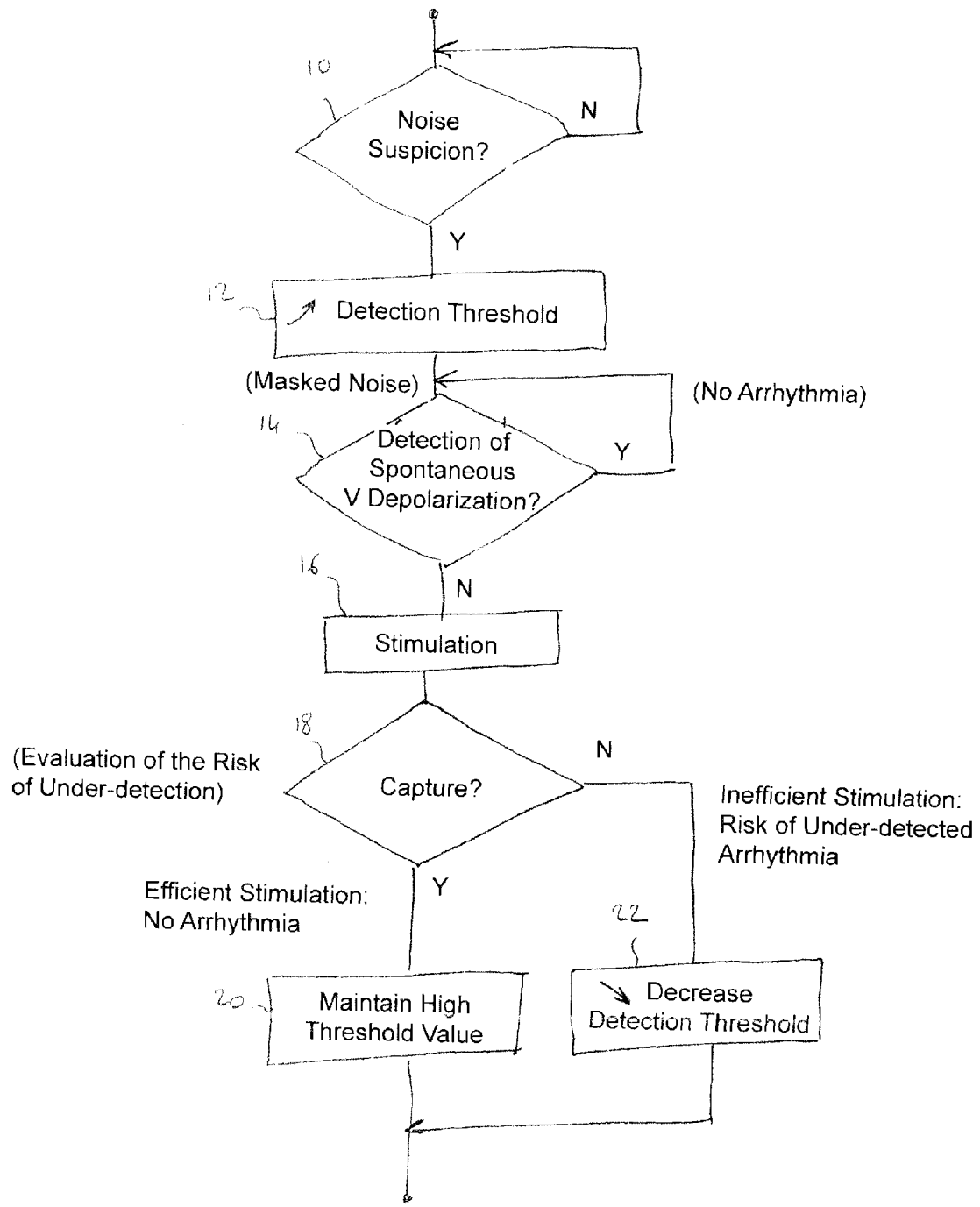
FIG. 3 is a flowchart of a process for detecting spontaneous ventricular events in a heart by using an implantable device according to an exemplary embodiment.

Exemplary devices and methods described here utilize techniques designed to safely lower the sensitivity (e.g., for better noise immunity) while maintaining a good detection of arrhythmias. With reference to FIG. 3, a method is shown, according to one such embodiment, for detecting spontaneous ventricular events in a heart by using an implantable device. The first step (block 10) is a test of noise suspicion. Various known techniques may be used to test for whether noise is suspected to be present in measured data, such as those described in the following documents, all of which are assigned to Sorin CRM:

European Published Application No. 0838235 A1 and its counterpart U.S. Pat. No. 5,868,793, which describe an algorithm for detecting and classifying tachyarrhythmias notably implemented under the name PARAD/PARAD+ in the Ovatio and Paradym devices of Sorin CRM. When an arrhythmia is detected, the ventricular noise is suspected because of the presence of short cycles due to artifacts and not to a true arrhythmia.

European Published Application No. 1857142 A1 and its counterpart U.S. Pat. No. 7,968,068, which performs a double detection; that is, detection of the depolarization, by analyzing the EGM electrical signal, and detection of the contraction of the myocardium, by measuring the endocardial acceleration via an accelerometer in direct contact with the heart muscle. There is suspicion of noise when the device detects an electrical signal (noise sensitive) that is not followed by a contraction (mechanical phenomenon that is not affected by noise).

European Published Application No. 2368493 A1 and its counterpart United Stated Published Application No. 2011/0230776, which provide for simultaneous analysis of two different EGM channels, namely, those of an unipolar signal and of a bipolar signal. This is a two-dimensional analysis from the "cardiac loop" or VGM vectogram, which is the representation in a two-dimensional space of one of the two signals relative to the other. The morphological characteristics of the vectogram are analyzed to discriminate between effective depolarization and noise collected by the detection circuit.

In case of suspected noise, the detection threshold may be raised (block 12), which decreases the sensitivity. This increase may be gradual and steady, for example an increase of 0.2 mV every 16 ms as long as the retriggerable refractory period is present. The threshold may be raised to a level above the amplitude of the noise. In some embodiments, a target value of the detection threshold may be calculated by taking, for example, the average of the amplitudes for several (e.g., six) cycles detected as noisy. The new applied threshold may be set to this calculated average amplitude (e.g., limited to a maximum value).

Figure 4:
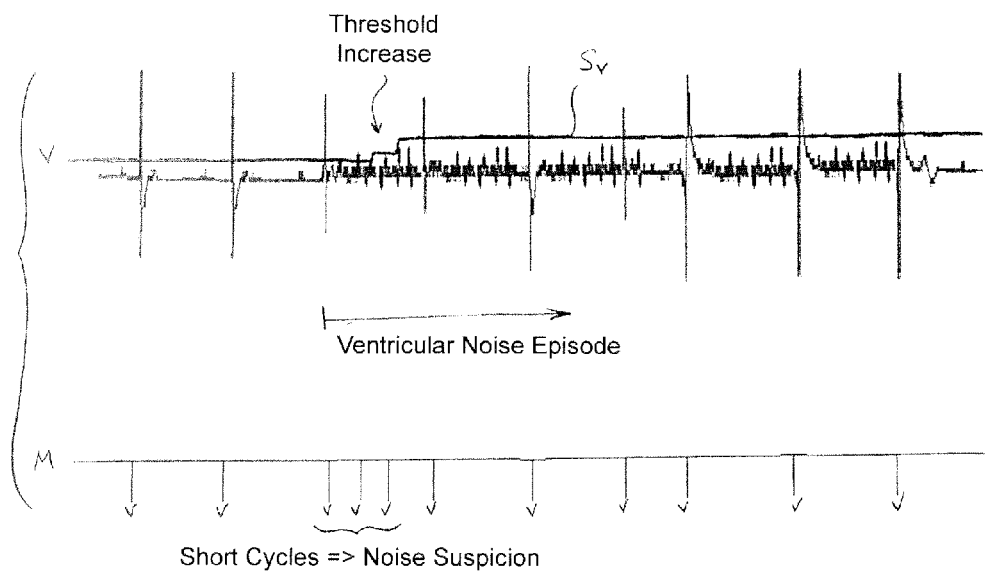
FIG. 4 is a set of timing diagrams illustrating the behavior of an implant at the onset of an episode of ventricular noise according to an exemplary embodiment.

The increase of the detection threshold may allow noise that was previously detected to be covered. FIG. 4 illustrates this situation, according to an exemplary embodiment. The occurrence of an episode of ventricular noise leads to the appearance of cycles detected as short (V marker), which is in fact composed of artifacts. The ventricular detection threshold $S_V$ is then increased, which has the effect of removing these artifacts. After the threshold is increased, only the markers corresponding to true ventricular depolarizations remain.

It is important that the noise thus masked does not lead to an under-detection. Increasing the detection threshold and reducing the sensitivity of the implant increases the risk of sub-detection of ventricular arrhythmia. The implant may detect a spontaneous ventricular depolarization (block 14). This means that there is no VF, because it is certain that this is a true depolarization above the level of noise. In some instances, the absence of spontaneous ventricular depolarization sensed at the end of the escape interval may lead the implant to apply a ventricle stimulation pulse (block 16). For instance, this can be a normal stimulation, required because of the patient's condition. In other instances, the stimulation may result from under-detection of ventricular arrhythmias (e.g., in case of low amplitude VF having an amplitude under the threshold that was noted in step 12).

To verify that in this case ventricular arrhythmia is not sub-detected, a capture test may be performed (block 18) on the stimulated cycle. This capture test can be performed according to one of various known methods, such as those described in the following documents, all of which are assigned to Sorin CRM S.A.S.:

Published PCT Application No. WO 93/02741 A1 (United States counterpart U.S. Pat. No. 5,411,533) and European Published Application No. 1287849 A1 (United States counterpart U.S. Pat. No. 6,714,820) by analysis of the collected electrical signals (e.g., analysis of the evoked response);

European Published Application No. 2324885 A1 (United States counterpart Published Application No. 2011/0118804) by analyzing the cardiac vectogram VGM from descriptor parameters of the non-temporal two-dimensional characteristic obtained;

European Published Application No. 2412401 A1 (United States counterpart Published Application No. US2012/0022607 "Ventricular capture testing by analysis of an endocardial acceleration signal in an active implantable medical device"): by detecting a mechanical activity in the heart following the stimulation.

Confirmation of capture means that the stimulation is effective and that the patient is not in cardiac arrhythmia. The implant then can maintain a reduced sensitivity (step 20), such as with the threshold at the raised level noted in step 12. The absence of capture indicates that the stimulation is not effective, presumably due to arrhythmia in progress. To avoid undersensing or sub-detection of this arrhythmia, the implant may increase the detection sensitivity (step 22) by lowering the threshold. In various embodiments, the threshold may be lowered gradually (e.g., in 0.2 mV every 16 ms) down to the sensitivity programmed by the physician or directly to the desired sensitivity value.

Figure 5:
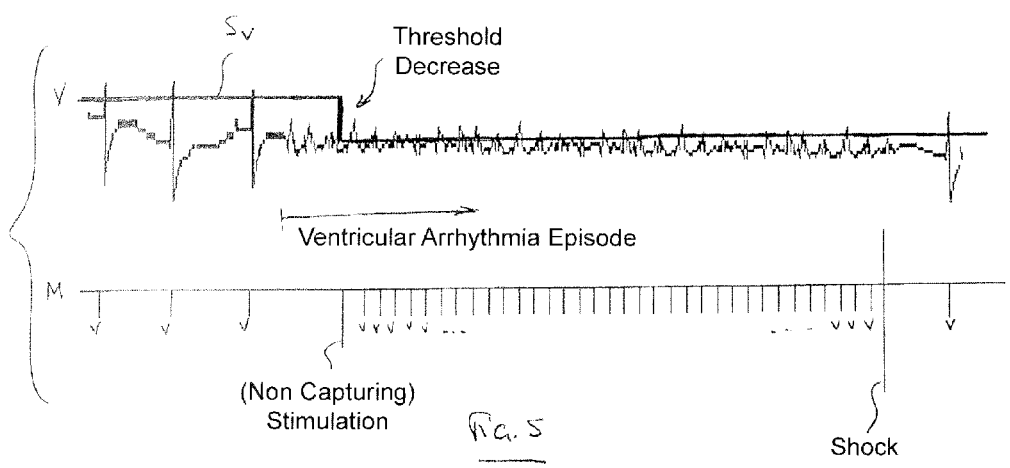
FIG. 5 is a set of timing diagrams illustrating the behavior of the implant in case of occurrence of an episode of low amplitude ventricular arrhythmia according to an exemplary embodiment.

FIG. 5 illustrates a timing diagram showing reduction of the detection threshold according to an exemplary embodiment. At the beginning of an episode of ventricular arrhythmia, the implant does not detect the regular rhythm of the ventricular depolarizations (V markers) and therefore triggers stimulation. Since this stimulation is not followed by capture, (e.g., as detected by a capture detection method such as one of the methods described above), the ventricular detection threshold SV then is lowered to a level that is sufficient to detect the electrical activity characteristic of the ventricular arrhythmia (e.g., a series of V markers at very short intervals). The lowering of the detection threshold may lead to the justified application of a defibrillation shock.

What is claimed is:

1. A method of detecting spontaneous ventricular events in a heart by using an implantable device, the method comprising:
    (A) using the implantable device to collect data relating to electrical activity of the heart;
    (B) applying a sensitivity function to the collected data to detect occurrence of ventricular events, wherein the sensitivity function is based on an adjustable detection threshold;
    (C) determining whether noise is suspected to be present in the collected data;
    (D) increasing the adjustable detection threshold upon determining that noise is suspected to be present in the collected data;
    (E) providing a stimulation pulse to the heart when a ventricular event has not occurred after a predetermined escape interval; and, following the stimulation pulse,
    (F) applying a capture test to detect whether an induced depolarization has occurred;
    (G) reducing the adjustable detection threshold when an induced depolarization is not detected based on the capture test; and
    (H) maintaining the adjustable detection threshold when an induced depolarization is detected based on the capture test.

2. The method of claim 1, further comprising (I) detecting whether arrhythmias are present in the ventricular events based on the collected data and, when arrhythmias are determined to be present in the ventricular events, (J) using the implantable device to apply antitachycardia therapy.

3. The method of claim 1, wherein increasing the adjustable detection threshold comprises gradually increasing the adjustable detection threshold in successive steps during a retriggerable refractory period.

4. The method of claim 1, wherein increasing the adjustable detection threshold comprises increasing the adjustable detection threshold to a level directly dependent on an amplitude of one or more cycles for which suspected noise has been detected.

5. The method of claim 1, wherein reducing the adjustable detection threshold comprises gradually reducing the adjustable detection threshold in successive steps down to a predetermined limit value.

6. The method of claim 1, wherein reducing the adjustable detection threshold comprises reducing the adjustable detection threshold directly to a predetermined limit value.

7. An implantable device configured to detect spontaneous ventricular events in a heart, the implantable device comprising:
    a processor and
    a memory having instructions stored thereon that, when executed by the processor, cause the processor to:
        (A) collect data relating to electrical activity of the heart;
        (B) apply a sensitivity function to the collected data to detect occurrence of ventricular events wherein the sensitivity function is based on an adjustable detection threshold;
        (C) determine whether noise is suspected to be present in the collected data;
        (D) increase the adjustable detection threshold upon determining that noise is suspected to be present in the collected data;

(E) provide a stimulation pulse to the heart when a ventricular event has not occurred after a predetermined escape interval; and, following the stimulation pulse, (F) apply a capture test to detect whether an induced depolarization has occurred;

(G) reduce the adjustable detection threshold when an induced depolarization is not detected based on the capture test; and (H) maintain the adjustable detection threshold when an induced indicated depolarization is detected based on the capture test.

8. The implantable device of claim 7, wherein the memory has instructions stored thereon that, when executed by the processor, further cause the processor to (I) detect whether arrhythmias are present in the ventricular events based on the collected data and, when arrhythmias are determined to be present in the ventricular events, (J) use the implantable device to apply antitachycardia therapy.

9. The implantable device of claim 7, wherein the processor is configured to gradually increase the adjustable detection threshold in successive steps during a retriggerable refractory period.

10. The implantable device of claim 7, wherein the processor is configured to increase the adjustable detection threshold to a level directly dependent on an amplitude of one or more cycles for which suspected noise has been detected.

11. The implantable device of claim 7, wherein the processor is configured to gradually reduce the adjustable detection threshold in successive steps down to a predetermined limit value.

12. The implantable device of claim 7, wherein the processor is configured to reduce the adjustable detection threshold directly to a predetermined limit value.

13. A processor-readable storage medium having instructions stored thereon that, when executed by a processor of an implantable device, cause the implantable device to implement operations that comprise:

(A) using the implantable device to collect data relating to electrical activity of the heart;

(B) applying a sensitivity function to the collected data to detect occurrence of ventricular events, wherein the sensitivity function is based on an adjustable detection threshold;

(C) determining whether noise is suspected to be present in the collected data; and (D) increasing the adjustable detection threshold upon determining that noise is suspected to be present in the collected data, (E) providing a stimulation pulse to the heart when a ventricular event has not occurred after a predetermined escape interval; and, following the stimulation pulse, (F) applying a capture test to detect whether an induced depolarization has occurred;

(G) reducing the adjustable detection threshold when an induced depolarization is not detected based on the capture test; and (H) maintaining the adjustable detection threshold when an induced indicated depolarization is detected based on the capture test.

14. The processor-readable storage medium of claim 13, wherein the operations further comprise:

(I) detecting whether arrhythmias are present in the ventricular events based on the collected data and, when arrhythmias are determined to be present in the ventricular events, (J) using the implantable device to apply antitachycardia therapy.

15. The processor-readable storage medium of claim 13, wherein increasing the adjustable detection threshold comprises gradually increasing the adjustable detection threshold in successive steps during a retriggerable refractory period.

16. The processor-readable storage medium of claim 13, wherein increasing the adjustable detection threshold comprises increasing the adjustable detection threshold to a level directly dependent on an amplitude of one or more cycles for which suspected noise has been detected.

17. The processor-readable storage medium of claim 13, wherein reducing the adjustable detection threshold comprises gradually reducing the adjustable detection threshold in successive steps down to a predetermined limit value.

18. The processor-readable storage medium of claim 13, wherein reducing the adjustable detection threshold comprises reducing the adjustable detection threshold directly to a predetermined limit value.

\* \* \* \* \*